United States Patent [19]

Hoffmann et al.

[11] 4,126,677

[45] Nov. 21, 1978

[54] O,S-DIALKYL-O-(1-CYANOALKYL-3-SUBSTITUTED)-PYRAZOL(5)YL-THIONOTHIOLPHOSPHORIC ACID ESTERS

[75] Inventors: Hellmut Hoffmann, Wuppertal; Ingeborg Hammann, Cologne, both of Germany

[73] Assignee: Bayer Aktiengesellschaft, Leverkusen, Germany

[21] Appl. No.: 768,504

[22] Filed: Feb. 14, 1977

[30] Foreign Application Priority Data

Mar. 3, 1976 [DE] Fed. Rep. of Germany ....... 2608643

[51] Int. Cl.$^2$ ............................ A01N 9/36; C07F 9/65
[52] U.S. Cl. ................................... 424/200; 548/376; 548/377; 548/375
[58] Field of Search ................. 548/376, 377; 424/273, 424/200; 548/375

[56] References Cited

U.S. PATENT DOCUMENTS

| 3,825,557 | 7/1974 | Hoffmann et al. ............ 548/376 |
| 3,843,679 | 10/1974 | Hoffmann et al. ............ 424/200 |

FOREIGN PATENT DOCUMENTS 713,278  4/1952  United Kingdom ............ 544/337

OTHER PUBLICATIONS

Hoffmann et al. Chem. Abs. vol. 74, 1971, 142065b.

*Primary Examiner*—Natalie Trousof
*Assistant Examiner*—Jane T. Fan
*Attorney, Agent, or Firm*—Sprung, Felfe, Horn, Lynch & Kramer

[57] ABSTRACT

O,S-Dialkyl-O-(1-cyanoalkyl-3-substituted)-pyrazol-(5)yl-thionothiolphosphoric acid esters of the formula $$\begin{array}{c} R^4 \quad\quad R^3 \\ RO\;\;S \\ \;\;\;\diagdown\;\| \\ \;\;\;\;\;P-O \\ \;\;\;\diagup \\ R^1S \quad\quad N-N \\ \quad\quad\quad | \\ \quad\quad\quad R^2 \end{array} \quad (I)$$

in which

R and R$^1$ each independently is alkyl with 1 to 6 carbon atoms,

R$^2$ is cyanoalkyl with 1 to 4 carbon atoms in the alkyl moiety,

R$^3$ is alkyl with 1 to 4 carbon atoms or carbalkoxy with 1 to 4 carbon atoms in the alkoxy moiety, and R$^4$ is hydrogen or halogen, which possess arthropodicidal properties.

10 Claims, No Drawings

O,S-DIALKYL-O-(1-CYANOALKYL-3-SUBSTITUTED)-PYRAZOL(5)YL-THIONOTHIOLPHOSPHORIC ACID ESTERS

The present invention relates to and has for its objects the provision of particular new O,S-dialkyl-O-(1-cyanoalkyl-3-substituted)-pyrazol(5)yl-thionothiolphosphoric acid esters, e.g., O,S-dialkyl-O-(1-cyanoalkyl-3-alkyl- or -3-carbalkoxy)-pyrazol(5)yl-thionothiolphosphoric acid esters optionally halogen-substituted in the 4-position, which possess arthropodicidal properties, active compositions in the form of mixtures of such compounds with solid and liquid dispersible carrier vehicles, and methods for producing such compounds and for using such compounds in a new way especially for combating pests, e.g., arthropods, with other and further objects becoming apparent from a study of the within specification and accompanying examples.

It has been disclosed in U.S. Pat. Nos. 2,754,244 and 3,843,679 that pyrazolothionophosphoric acid esters, for example O,O-dimethyl-O-[3-carboethoxy-4-chloro-1-methyl-pyrazol(5)yl]-(Compound A) or O,O-diethyl-O-[3-methyl-(Compound B) or -3-carboethoxy-1-methyl-4-methyl-(Compound C) or -3-carboethoxy-4-chloro-1-(2-cyanoethyl)-pyrazol(5)yl]-thionophosphoric acid ester (Compound D), possess insecticidal and acaricidal properties.

The present invention provides O,S-dialkyl-O-pyrazoledithiophosphoric acid esters of the general formula

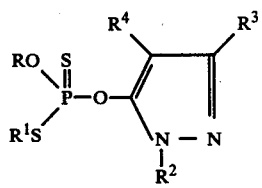

in which
R and $R^1$ each independently is alkyl with 1 to 6 carbon atoms,
$R^2$ is cyanoalkyl with 1 to 4 carbon atoms in the alkyl moiety,
$R^3$ is alkyl with 1 to 4 carbon atoms or carbalkoxy with 1 to 4 carbon atoms in the alkoxy moiety, and
$R^4$ is hydrogen or halogen.

Preferably, R represents straight chain or branched alkyl with 1 to 4, especially 1 to 3 carbon atoms, $R^1$ represents straight-chain or branched alkyl with 1 to 5, especially 1 to 4, carbon atoms, $R^2$ represents 2-cyanoethyl or 2-cyano-n-propyl, $R^3$ represents straight-chain or branched alkyl with 1 to 3 carbon atoms, especially methyl, or carbalkoxy with 1 to 3 carbon atoms in the alkoxy part, especially carboethoxy, and $R^4$ represents hydrogen or chlorine.

The invention also provides a process for the preparation of a O,S-dialkyl-O-pyrazoledithiophosphoric acid ester of the formula (I) in which a 1-cyanoalkyl-5-hydroxy-pyrazole derivative of the formula

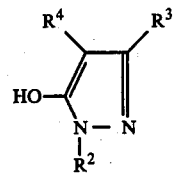

in which
$R^2$, $R^3$ and $R^4$ have the above-mentioned meanings, is reacted, optionally in the presence of an acid acceptor or in the form of an alkali metal salt, alkaline earth metal salt or ammonium salt, with a O,S-dialkyl-dithiophosphoric acid diester halide of the formula

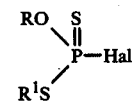

in which
R and $R^1$ have the abovementioned meanings and hal represents halogen, preferably chlorine, optionally in the presence of a solvent.

Surprisingly, the O,S-dialkyl-O-pyrazolodithiophosphoric acid esters according to the invention possess a better insecticidal and acaricidal action than the known compounds of analogous structure and of the same type of action. The compounds of the present invention thus represent a genuine enrichment of the art.

If, for example, O-ethyl-S-n-propyl-thionothiolphosphoric acid diester chloride and 4-chloro-1-(2-cyano-n-propyl)-5-hydroxy-3-methyl-pyrazole are used as starting materials, the course of the reaction can be represented by the following formula scheme

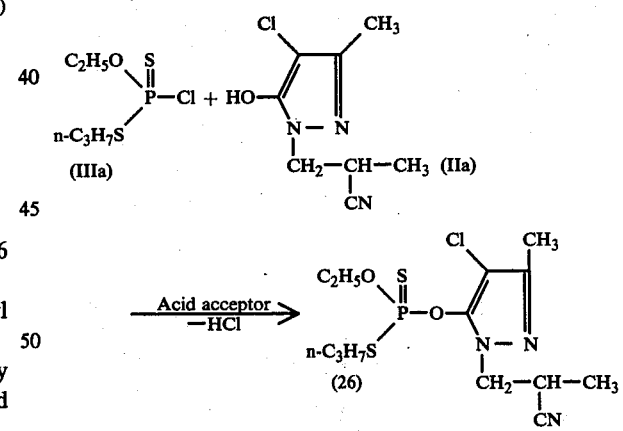

The 1-cyanoalkyl-5-hydroxy-pyrazole derivatives (II) to be used as starting materials are disclosed in U.S. Pat. No. 3,843,679 and published Netherlands patent application No. 7,209,051, as are the O,S-dialkyldithiophosphoric acid diester halides (III) in USSR patent specification No. 184,863.

The following may be mentioned individually as examples of the 1-cyanoalkyl-5-hydroxypyrazole derivatives: 1-(2-cyanoethyl)-3-methyl-, 1-(2-cyano-n-propyl)-3-methyl-, 3-carbomethoxy-1-(2-cyanoethyl)-, 3-carboethoxy-1-(2-cyanoethyl)-, 3-carbo-n-propoxy-1-(2-cyanoethyl)-, 3-carbomethoxy-1-(2-cyano-n-propyl)-, 3-carboethoxy-1-(2-cyano-n-propyl)-, 3-carbo-n-propoxy-1-(2-cyano-n-propyl)-, 4-chloro-1-(2-cyanoethyl)-3-methyl-, 4-chloro-1-(2-cyano-n-propyl)-3-methyl-, 3-carbomethoxy-4-chloro-1-(2-cyanoethyl)-, 3-carboethoxy-4-chloro-1-(2-cyanoethyl)-, 3-carbo-n-propoxy-4-chloro-1-(2-cyanoethyl)-, 3-carbomethoxy-4-chloro-1-(2-cyano-n-propyl)-, 3-carboethoxy-4-chloro-1-(2-cyano-n-propyl)- and 3-carbo-n-propoxy-4-chloro-1-(2-cyano-n-propyl)-5-hydroxypyrazole.

The following may be mentioned individually as examples of the O,S-dialkyldithiophosphoric acid diester halides: O-methyl-S-methyl-, O-methyl-S-ethyl-, O-methyl-S-n-propyl-, O-methyl-S-iso-propyl-, O-methyl-S-n-butyl-, O-methyl-S-sec.-butyl-, O-methyl-S-iso-butyl-, O-ethyl-S-methyl-, O-ethyl-S-ethyl-, O-ethyl-S-n-propyl-, O-ethyl-S-iso-propyl-, O-ethyl-S-n-butyl-, O-ethyl-S-iso-butyl-, O-ethyl-S-sec.-butyl-, O-n-propyl-S-ethyl-, O-n-propyl-S-n-propyl, O-n-propyl-S-iso-propyl-, O-n-propyl-S-n-butyl-, O-n-propyl-S-iso-butyl-, O-n-propyl-S-sec.-butyl-, O-iso-propyl-S-ethyl-, O-iso-propyl-S-n-propyl-, O-iso-propyl-S-iso-propyl-, O-iso-propyl-S-n-butyl-, O-iso-propyl-S-iso-butyl- and O-iso-propyl-S-sec.-butyldithiophosphoric acid diester chloride.

The reaction of the process for the preparation of the compounds according to the invention is preferably carried out in the presence of a solvent or diluent. Practically all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0° to 120° C, preferably at 20° to 70° C.

In general, the reaction is allowed to take place under normal pressure.

In carrying out the process, the starting components are preferably employed in equimolar ratios. An excess of one or other reactant produces no essential advantages. The reaction is preferably carried out in one of the stated solvents in the presence of an acid acceptor, at the stated temperature. After the reaction has ended, the reaction mixture may be cooled, poured into water and extracted by shaking with an organic solvent, for example methylene chloride. The organic phase may be worked up in the usual manner by washing, drying and distilling off the solvent.

The new compounds are obtained in the form of oils which in some cases cannot be distilled without decomposition, but which are freed from the last volatile constituents by so-called "slight distillation," that is to say prolonged heating under reduced pressure to moderately elevated temperatures, and are purified in this way. They are characterized by the refractive index.

As already mentioned, the O,S-dialkyl-O-pyrazoledithiophosphoric acid esters according to the invention are distinguished by an excellent insecticidal and acaricidal activity. They are active against plant pests, hygiene pests and pests of stored products, and against parasites (ectoparasites) in the veterinary medicine field. They possess a low phytotoxicity and a good action against both sucking and biting insects and mites.

For this reason, the compounds according to the invention can be employed successfully as pesticides in plant protection, as well as in hygiene protection and protection of stored products and in the veterinary field.

The active compounds are well tolerated by plants, have a favorable level of toxicity to warm-blooded animals, and can be used for combating animal pests, especially insects, arachnida and nematodes, which are encountered in agriculture, in forestry, in the protection of stored products and of materials, and in the hygiene field. They are active against normally sensitive and resistant species and against all or some stages of development. The above-mentioned pests include:

From the order of the *Isopoda*, for example *Oniscus asellus*, *Armadillidium vulgare* and *Porcellio scaber*; from the order of the *Diplopoda*, for example *Blaniulus guttulatus*; from the order of the *Chilopoda*, for example, *Geophilus carpophagus* and *Scutigera* spec.; from the order of the *Symphyla*, for example *Scutigerella immaculata*; from the order of the *Thysanura*, for example *Lepisma saccharina*; from the order of the *Collembola*, for example *Onychiurus armatus*; from the order of the *Orthoptera*, for example *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria*; from the order of the *Dermaptera*, for example *Forficula auricularia*; from the order of the *Isoptera*, for example *Reticulitermes* spp.; from the order of the *Anoplura*, for example *Phylloxera vastatrix*, *Pemphigus* spp., *Pediculus humanus corporis*, *Haematopinus* spp. and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci*; from the order of the *Heteroptera*, for example *Eurygaster* spp., *Dysderous intermedius*, *Piesma quadrata*, *Cimex lectularius*, *Rhodnius prolixus* and *Triatoma* spp.; from the order of the *Hompotera*, for example *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomi*, *Eriosoma lanigerum*, *Hyalopterus arundinis*, *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.; from the order of the *Lepidoptera*, for example *Pectinophora gossypiella*, *Bupalus piniarius*, *Cheimatobia brumata*, *Lithiocolletis blancardella*, *Hyponomeuta padella*, *Plutella maculipennis*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Laphygma exigua*, *Mamestra brassicae*, *Panolis flammea*, *Prodenia litura*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Cacoecia podana*, *Capua reticulana*, *Choristoneura fumiferana*, *Clysia ambiguella*, *Homona magnanima* and *Tortrix viridana*; from the order of the Coleoptera, for example *Anobium punctatum*, *Rhizopertha*

*dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera,* for example *Diprion* spp., *Hoplocampa* spp., *Lasius* spp., *Monomorium pharaonis* and *Vespa* spp.; from the order of the *Diptera,* for example, *Aedes* spp., *Anopheles* spp., *Culex* spp., *Drosophila melanogaster, Musca* spp., Fannia spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera,* for example *Xenopsylla cheopis* and *Ceratophyllus* spp.; from the order of the *Arachnida,* for example *Scorpio maurus* and *Latrodectus mactans;* from the order of the *Acarina,* for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g, ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20–100% by weight of the active compound.

Furthermore, the present invention contemplates methods of selectively killing, combating or controlling pests, e.g., arthropods and especially insects and acarids, which comprises applying to at least one of correspondingly (a) such insects, (b) such acarids, and (c) the corresponding habitat thereof, i.e., the locus to be protected, e.g., to a growing crop, to an area where a crop is to be grown or to a domestic animal, a correspondingly combative or toxic amount, i.e., an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all the caterpillars were killed whereas 0% meant that none of the caterpillars were killed.

The active compounds, the concentrations of the active compounds, the evaluation times and the results can be seen from the following Table 1:

Table 1

| Active compound | Active compound concentration in % | Degree of destruction in % after 3 days |
|---|---|---|
| (Plutella test) | | |
| $(C_2H_5O)_2P(S)-O-$ pyrazole with $CH_3$, $CO-OC_2H_5$, $CH_3$ (known) (c) | 0.1<br>0.01 | 100<br>0 |
| n-$C_3H_7S$, $CH_3O$, $P(S)-O-$ pyrazole with Cl, $CH_3$, $CH_2-CH_2-CN$ (11) | 0.1<br>0.01 | 100<br>100 |
| n-$C_3H_7S$, $C_2H_5O$, $P(S)-O-$ pyrazole with $CH_3$, $CH_2-CH_2-CN$ (3) | 0.1<br>0.01 | 100<br>100 |
| n-$C_3H_7S$, $C_2H_5O$, $P(S)-O-$ pyrazole with Cl, $CH_3$, $CH_2-CH_2-CN$ (10) | 0.1<br>0.01 | 100<br>100 |
| n-$C_3H_7S$, $C_2H_5O$, $P(S)-O-$ pyrazole with $CO-OC_2H_5$, $CH_2-CH_2-CN$ (13) | 0.1<br>0.01 | 100<br>100 |
| n-$C_3H_7S$, $C_2H_5O$, $P(S)-O-$ pyrazole with Cl, $CO-OC_2H_5$, $CH_2-CH_2-CN$ (15) | 0.1<br>0.01 | 100<br>100 |
| n-$C_4H_9S$, $C_2H_5O$, $P(S)-O-$ pyrazole with Cl, $CH_3$, $CH_2-CH_2-CN$ (9) | 0.1<br>0.01 | 100<br>100 |

Table 1-continued
(Plutella test)

| Active compound | Active compound concentration in % | Degree of destruction in % after 3 days |
|---|---|---|
| (14) n-C$_4$H$_9$S(S)P(OC$_2$H$_5$)–O–[pyrazole with CO–OC$_2$H$_5$; N–CH$_2$–CH$_2$–CN] | 0.1<br>0.01 | 100<br>100 |
| (2) n-C$_3$H$_7$S(S)P(O-n-C$_3$H$_7$)–O–[pyrazole with CH$_3$; N–CH$_2$–CH$_2$–CN] | 0.1<br>0.01 | 100<br>100 |
| (7) n-C$_3$H$_7$S(S)P(O-n-C$_3$H$_7$)–O–[pyrazole with Cl, CH$_3$; N–CH$_2$–CH$_2$–CN] | 0.1<br>0.01 | 100<br>100 |
| (23) n-C$_3$H$_7$S(S)P(O-iso-C$_3$H$_7$)–O–[pyrazole with CH$_3$; N–CH$_2$–CH$_2$–CN] | 0.1<br>0.01 | 100<br>100 |
| (16) n-C$_4$H$_9$S(S)P(OC$_2$H$_5$)–O–[pyrazole with Cl, CO$_2$–C$_2$H$_5$; N–CH$_2$–CH$_2$–CN] | 0.0<br>0.01 | 100<br>100 |
| (1) n-C$_3$H$_7$S(S)P(OC$_2$H$_5$)–O–[pyrazole with CH$_3$; N–CH$_2$–CH(CN)–CH$_3$] | 0.1<br>0.01 | 100<br>100 |
| (20) n-C$_3$H$_7$S(S)P(OC$_2$H$_5$)–O–[pyrazole with CO–OC$_2$H$_5$; N–CH$_2$–CH(CN)–CH$_3$] | 0.1<br>0.01 | 100<br>100 |
| (22) n-C$_3$H$_7$S(S)P(OC$_2$H$_5$)–O–[pyrazole with Cl, CO–OC$_2$H$_5$; N–CH$_2$–CH(CN)–CH$_3$] | 0.1<br>0.01 | 100<br>100 |
| (18) n-C$_4$H$_9$S(S)P(OC$_2$H$_5$)–O–[pyrazole with CH$_3$; N–CH$_2$–CH(CN)–CH$_3$] | 0.1<br>0.01 | 100<br>100 |
| (19) n-C$_4$H$_9$S(S)P(OC$_2$H$_5$)–O–[pyrazole with CO–OC$_2$H$_5$; N–CH$_2$–CH(CN)–CH$_3$] | 0.1<br>0.01 | 100<br>100 |

EXAMPLE 2

Myzus test (contact action)

Solvent: 3 parts by weight of acetone

Emulsifier: 1 part by weight of alkylarylpolyglycol ether

To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which had been heavily infested with peach aphids (Myzus persicae) were sprayed with the preparation of the active compound until dripping wet.

After the specified periods of time, the degree of destruction was determined as a percentage: 100% meant that all the aphids were killed whereas 0% meant that none of the aphids were killed.

The active compounds, the concentrations of the active compounds, the evaluation times and the results can be seen from the following Table 2:

Table 2

(*Myzus* test)

| Active compound | Active compound concentration in % | Degree of destruction in % after 1 day |
|---|---|---|
| (B) (C₂H₅O)₂P(=S)-O-[pyrazole with CH₃, NH] (known) | 0.1 / 0.01 / 0.001 | 99 / 40 / 0 |
| (A) (CH₃O)₂P(=S)-O-[pyrazole with Cl, CO-OC₂H₅, N-CH₃] (known) | 0.1 / 0.01 / 0.001 | 97 / 40 / 0 |
| (D) (C₂H₅O)₂P(=S)-O-[pyrazole with Cl, CO-OC₂H₅, N-CH₂-CH₂-CN] (known) | 0.1 / 0.01 | 40 / 0 |
| (11) n-C₃H₇S, CH₃O, P(=S)-O-[pyrazole with Cl, CH₃, N-CH₂-CH₂-CN] | 0.1 / 0.01 / 0.001 | 100 / 100 / 70 |
| (3) n-C₃H₇S, C₂H₅O, P(=S)-O-[pyrazole with CH₃, N-CH₂-CH₂-CN] | 0.1 / 0.01 / 0.001 | 100 / 98 / 95 |
| (10) n-C₃H₇S, C₂H₅O, P(=S)-O-[pyrazole with Cl, CH₃, N-CH₂-CH₂-CN] | 0.1 / 0.01 / 0.001 | 100 / 100 / 100 |
| (13) n-C₃H₇S, C₂H₅O, P(=S)-O-[pyrazole with CO-OC₂H₅, N-CH₂-CH₂-CN] | 0.1 / 0.01 / 0.001 | 100 / 100 / 70 |
| (7) n-C₃H₇S, n-C₃H₇O, P(=S)-O-[pyrazole with Cl, CH₃, N-CH₂-CH₂-CN] | 0.1 / 0.01 / 0.001 | 100 / 100 / 70 |
| (8) n-C₃H₇S, iso-C₃H₇O, P(=S)-O-[pyrazole with Cl, CH₃, N-CH₂-CH₂-CN] | 0.1 / 0.01 / 0.001 | 100 / 100 / 70 |
| (1) n-C₃H₇S, C₂H₅O, P(=S)-O-[pyrazole with CH₃, N-CH₂-CH(CN)-CH₃] | 0.1 / 0.01 / 0.001 | 100 / 100 / 99 |
| (20) n-C₃H₇S, C₂H₅O, P(=S)-O-[pyrazole with CO-OC₂H₅, N-CH₂-CH(CN)-CH₃] | 0.1 / 0.01 / 0.001 | 100 / 99 / 70 |

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following Table 3:

Table 3
(Tetranychus test)

| Active compound | Active compound concentration in % | Degree of destruction in % after 1 day |
|---|---|---|
| (C₂H₅O)₂P(S)-O-[pyrazole with CH₃, CO-OC₂H₅, N-CH₃] (known) (C) | 0.1 | 0 |
| (CH₃O)₂P(S)-O-[pyrazole with Cl, CO-OC₂H₅, N-CH₃] (known) (A) | 0.1 | 0 |
| (C₂H₅O)₂P(S)-O-[pyrazole with Cl, CO-OC₂H₅, N-CH₂-CH₂-CN] (known) (D) | 0.1 | 0 |
| n-C₃H₇S,CH₃O-P(S)-O-[pyrazole with Cl, CH₃, N-CH₂-CH₂-CN] (11) | 0.1 | 99 |
| n-C₃H₇S,C₂H₅O-P(S)-O-[pyrazole with CH₃, N-CH₂-CH₂-CN] (3) | 0.1 | 98 |
| n-C₃H₇S,C₂H₅O-P(S)-O-[pyrazole with Cl, CH₃, N-CH₂-CH₂-CN] (10) | 0.1 | 100 |
| n-C₄H₉S,C₂H₅O-P(S)-O-[pyrazole with Cl, CH₃, N-CH₂-CH₂-CN] (9) | 0.1 | 99 |

Table 3-continued
(Tetranychus test)

| Active compound | Active compound concentration in % | Degree of destruction in % after 1 day |
|---|---|---|
| n-C₃H₇S,C₂H₅O-P(S)-O-[pyrazole with CH₃, CN, N-CH₂-CH(CH₃)] (1) | 0.1 | 100 |
| n-C₄H₉S,C₂H₅O-P(S)-O-[pyrazole with CH₃, CN, N-CH₂-CH(CH₃)] (17) | 0.1 | 100 |

The following further examples are set forth to illustrate, without limitation, the manner of producing the instant compounds according to the present invention.

EXAMPLE 4

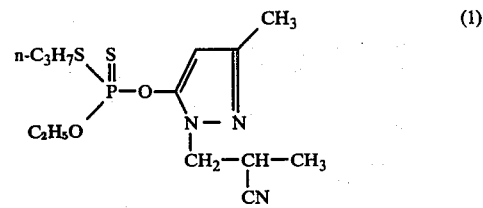
(1)

22 g (0.1 mol) of O-ethyl-S-n-propylthionothiolphosphoric acid diester chloride were poured into a suspension of 17 g (0.1 mol) of 1-(2-cyano-n-propyl)-3-methyl-5-hydroxypyrazole and 15 g of potassium carbonate, the reaction mixture was stirred further for 3 hours at 60° C and was cooled, and the batch was poured into water and extracted by shaking with methylene chloride. The organic phase was washed with twice 500 ml of water, dried over sodium sulfate and subjected to "slight distillation," under reduced pressure. 28 g (81% of theory) of O-ethyl-S-n-propyl-O-[1-(2-cyano-n-propyl)-3-methyl-pyrazol(5)yl]-thionothiolphosphoric acid ester of refractive index $n_D^{22}$: 1.5231 were obtained.

The following compounds of the formula

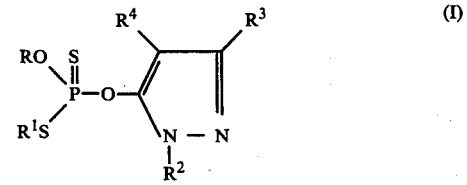
(I)

were prepared analogously:

Table 4

| Compound No. | R | R¹ | R² | R³ | R⁴ | Physical data (Refractive index) |
|---|---|---|---|---|---|---|
| 2 | n-C₃H₇— | n-C₃H₇— | —CH₂—CH₂—CN | —CH₃ | H | $n_D^{28}$: 1.5230 |
| 3 | C₂H₅— | n-C₃H₇— | —CH₂—CH₂—CN | —CH₃ | H | $n_D^{28}$: 1.5278 |
| 4 | iso-C₃H₇— | n-C₄H₉— | —CH₂—CH₂—CN | —CH₃ | H | $n_D^{28}$: 1.5185 |
| 5 | C₂H₅— | C₂H₅— | —CH₂—CH₂—CN | —CH₃ | H | $n_D^{21}$: 1.5376 |

Table 4-continued

| Compound No. | R | R¹ | R² | R³ | R⁴ | Physical data (Refractive index) |
|---|---|---|---|---|---|---|
| 6 | $C_2H_5-$ | $CH_3-$ | $-CH_2-CH_2-CN$ | $-CH_3$ | H | $n_D^{20}$: 1.5421 |
| 7 | $n-C_3H_7-$ | $n-C_3H_7-$ | $-CH_2-CH_2-CN$ | $-CH_3$ | Cl | $n_D^{25}$: 1.5263 |
| 8 | iso-$C_3H_7-$ | $n-C_3H_7-$ | $-CH_2-CH_2-CN$ | $-CH_3$ | Cl | $n_D^{25}$: 1.5260 |
| 9 | $C_2H_5-$ | $n-C_4H_9-$ | $-CH_2-CH_2-CN$ | $-CH_3$ | Cl | $n_D^{25}$: 1.5266 |
| 10 | $C_2H_5-$ | $n-C_3H_7-$ | $-CH_2-CH_2-CN$ | $-CH_3$ | Cl | $n_D^{22}$: 1.5292 |
| 11 | $CH_3-$ | $n-C_3H_7-$ | $-CH_2-CH_2-CN$ | $-CH_3$ | Cl | $n_D^{22}$: 1.5378 |
| 12 | $n-C_3H_7-$ | $CH_3-$ | $-CH_2-CH_2-CN$ | $-CH_3$ | Cl | $n_D^{22}$: 1.5345 |
| 13 | $C_2H_5-$ | $n-C_3H_7-$ | $-CH_2-CH_2-CN$ | $-CO-OC_2H_5$ | H | $n_D^{22}$: 1.5270 |
| 14 | $C_2H_5-$ | $n-C_4H_9-$ | $-CH_2-CH_2-CN$ | $-CO-OC_2H_5$ | H | $n_D^{22}$: 1.5258 |
| 15 | $C_2H_5-$ | $n-C_3H_7-$ | $-CH_2-CH_2-CN$ | $-CO-OC_2H_5$ | Cl | $n_D^{22}$: 1.5390 |
| 16 | $C_2H_5-$ | $n-C_4H_9-$ | $-CH_2-CH_2-CN$ | $-CO-OC_2H_5$ | Cl | $n_D^{22}$: 1.5351 |
| 17 | $C_2H_5-$ | $n-C_4H_9-$ | $-CH_2-CH(CN)-CH_3$ | $-CH_3$ | H | $n_D^{22}$: 1.5219 |
| 18 | $C_2H_5-$ | $C_2H_5-$ | $-CH_2-CH(CN)-CH_3$ | $-CH_3$ | H | $n_D^{22}$: 1.5240 |
| 19 | $C_2H_5-$ | $n-C_4H_9-$ | $-CH_2-CH(CN)-CH_3$ | $-CO-OC_2H_5$ | H | $n_D^{22}$: 1.5250 |
| 20 | $C_2H_5-$ | $n-C_3H_7-$ | $-CH_2-CH(CN)-CH_3$ | $-CO-OC_2H_5$ | H | $n_D^{20}$: 1.5278 |
| 21 | $C_2H_5-$ | $n-C_4H_9-$ | $-CH_2-CH(CN)-CH_3$ | $-CO-OC_2H_5$ | Cl | $n_D^{22}$: 1.5291 |
| 22 | $C_2H_5-$ | $n-C_3H_7-$ | $-CH_2-CH(CN)-CH_3$ | $-CO-OC_2H_5$ | Cl | $n_D^{20}$: 1.5325 |
| 23 | $i-C_3H_7-$ | $n-C_3H_7-$ | $-CH_2-CH_2-CN$ | $-CH_3$ | H | $n_D^{28}$: 1.5258 |

The following additional compounds of formula (I) can be similarly prepared:

Table 5

| Compound No. | R | R¹ | R² | R³ | R⁴ |
|---|---|---|---|---|---|
| 24 | $i-C_4H_5$ | $C_2H_5$ | $-CH_2-CH_2-CN$ | $-C_3H_7-h$ | H |
| 25 | $CH_3$ | $n-C_5H_{11}-$ | $-CH_2-CH_2-CN$ | $-CO-O-C_3H_7-n$ | H | and the like.

It will be appreciated that the instant specification and examples are set forth by way of illustration and not limitation, and that various modifications and changes may be made without departing from the spirit and scope of the present invention.

What is claimed is:

1. An O,S-dialkyl-O-(1-cyanoalkyl-3-substituted)-pyrazol(5)yl-thionothiol phosphoric acid ester of the formula

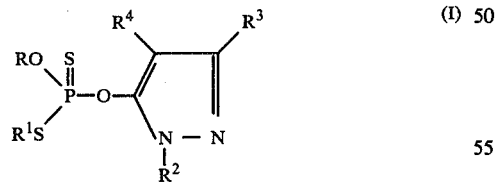

(I)

in which
R is alkyl with 1 or 2 carbon atoms,
R¹ is alkyl with 3 or 4 carbon atoms,
R² is cyanoalkyl with 1 to 4 carbon atoms in the alkyl moiety,
R³ is alkyl with 1 to 4 carbon atoms or carbalkoxy with 1 to 4 carbon atoms in the alkoxy moiety, and
R⁴ is hydrogen or halogen.

2. An ester according to claim 1 in which R is alkyl with 1 or 2 carbon atoms, R² is 2-cyanoethyl or 2-cyano-n-propyl, R³ is alkyl with 1 to 3 carbon atoms or carbalkoxy with 1 to 3 carbon atoms in the alkoxy moiety, and R⁴ is hydrogen or chlorine.

3. An ester according to claim 1 wherein such ester is O-ethyl-S-n-propyl-O-[1-(2-cyanoethyl)-3-methyl-pyrazol(5)yl]-thionothiolphosphoric acid ester of the formula

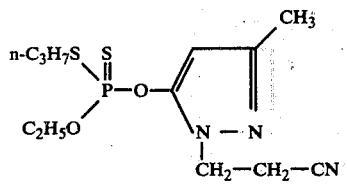

4. An ester according to claim 1 wherein such ester is O-ethyl-S-n-propyl-O-[1-(2-cyanoethyl)-3-methyl-4-chloro-pyrazol (5)yl]-thionothiolphosphoric acid ester of the formula

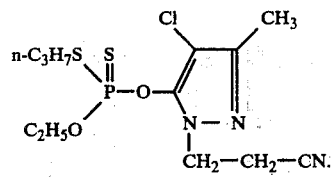

5. An ester according to claim 1 wherein such ester is O-ethyl-S-n-propyl-O-[1-(2-cyanoethyl)-3-carboethoxy-pyrazol(5)yl]-thionothiolphosphoric acid ester of the formula

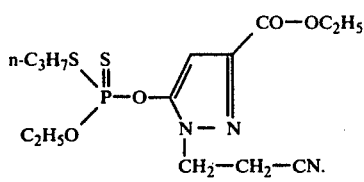

6. An ester according to claim 1 wherein such ester is O-ethyl-S-n-butyl-O-[1-(2-cyano-n-propyl)-3-methyl-pyrazol(5)yl]-thionothiolphosphoric acid ester of the formula

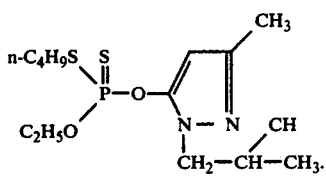

7. An ester according to claim 1 wherein such ester is O-ethyl-S-n-propyl-O-[1-(2-cyano-n-propyl)-3-carboethoxy-pyrazol-(5)yl]-thionothiolphosphoric acid ester of the formula

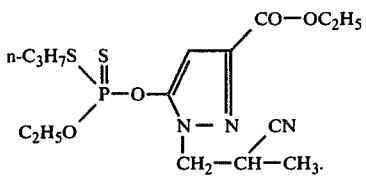

8. An arthropodicidal composition containing as active ingredient an arthropodicidally effective amount of an ester according to claim 1 in admixture with a diluent.

9. A method of combating arthropod pests which comprises applying to the pests or to a habitat thereof an arthropodicidally effective amount of an ester according to claim 1.

10. The method according to claim 9, in which said ester is

O-ethyl-S-n-propyl-O-[1-(2-cyanoethyl)-3-methyl-pyrazol-(5)yl]-thionothiolphosphoric acid ester, O-ethyl-S-n-propyl-O-[1-(2-cyanoethyl)-3-methyl-4-chloropyrazol-(5)yl]-thionothiolphosphoric acid ester, O-ethyl-S-n-propyl-O-[1-(2-cyanoethyl)-3-carboethoxypyrazol(5)yl]-thionothiolphosphoric acid ester, O-ethyl-S-n-butyl-O-[1-(2-cyano-n-propyl)-3-methyl-pyrazol(5)yl]-thionothiolphosphoric acid ester, or O-ethyl-S-n-propyl-O-[1-(2-cyano-n-propyl)-3-carboethoxypyrazol(5)yl]-thionothiolphosphoric acid ester.

* * * * *

UNITED STATES PATENT AND TRADEMARK OFFICE
CERTIFICATE OF CORRECTION

PATENT NO. : 4,126,677
DATED : November 21, 1978
INVENTOR(S) : Hoffmann et al

It is certified that error appears in the above-identified patent and that said Letters Patent are hereby corrected as shown below:

Col. 1, line 54          Insert -- - -- after "straight".

Col. 4, lines 45,46    Cancel "Hompotera", substitute --Homoptera--
Col. 4, lines 56,57    Cancel "Lithi-", substitute --Lith- --.
Col. 5, line 16        Cancel "Aedes", substitute --Aëdes--.
Col. 15, Table 5, sub-col. R, #24    Cancel "i-$C_4H_5$", substitute --i-$C_4H_9$--.
Col. 15, Table 5, sub-col. $R_3$, #24    Cancel "-$C_3H_7$-h", substitute -- -$C_3H_7$-n--.
Col. 15, Table 5, #25    move "H" to column "$R_4$".
Col. 17, line 24    Cancel "$CH_2$-CH(CH)-$CH_3$", substitute --$CH_2$-CH(CN)-$CH_3$--.

Signed and Sealed this

Seventeenth Day of July 1979

[SEAL]

Attest:

LUTRELLE F. PARKER
*Attesting Officer*     *Acting Commissioner of Patents and Trademarks*